United States Patent [19]
Cox

[11] 3,976,062
[45] Aug. 24, 1976

[54] METHOD OF APPLYING ORTHOPEDIC SPLINTS

[75] Inventor: Mervyn K. Cox, St. George, Utah

[73] Assignee: Mervyn K. Cox, Dr., St. George, Utah

[22] Filed: Apr. 21, 1975

[21] Appl. No.: 570,270

[52] U.S. Cl. .............................. 128/87 R; 128/89 R
[51] Int. Cl.² ........................................ A61F 5/04
[58] Field of Search ............... 128/87, 88, 89, 90, 128/83

[56] References Cited
UNITED STATES PATENTS

| | | | |
|---|---|---|---|
| 67,493 | 8/1867 | Burch | 128/87 R |
| 310,184 | 1/1885 | Davis | 128/88 |
| 739,634 | 9/1903 | Allen | 128/87 R |
| 1,741,011 | 12/1929 | Carvill | 128/87 R |
| 2,753,864 | 7/1956 | Weidemann, Jr. | 128/87 R |
| 3,036,831 | 5/1962 | Engan | 128/89 R |

*Primary Examiner*—John D. Yasko
*Attorney, Agent, or Firm*—Mallinckrodt & Mallinckrodt

[57] ABSTRACT

Method and means for orthopedic splinting or bracing comprise materials and procedures for straitjacketing body portions with one or more series of elongate splints of a relatively rigid plastic material in mutually spaced relationship so the splints extend longitudinally of the body part or parts concerned. Bands of perforated plastic material are applied transversely of and about the series of splints and are secured thereto to hold them in place. In those instances in which the splinting is above and below a joint, hinge means may be secured to the respective straitjacket structures to enable effective use of the joint during convalescence.

7 Claims, 10 Drawing Figures

METHOD OF APPLYING ORTHOPEDIC SPLINTS

BACKGROUND OF THE INVENTION

1. Field

The invention relates to means and methods for forming surgical and orthopedic supports.

2. State of the Art

Casts of plaster of Paris are widely used in stabliization of broken bones during healing and in sustaining traction, pull, counter-traction or counter-pull during orthopedic treatment. Rigid splints have also been used in stabilization of broken bones during healing.

Many shortcomings are known in the use of either rigid splints or plaster of Paris casts. Splints are awkward and apply pressure to the body where it is neither appropriate nor desirable. Further, there is no way of applying the splints so as to provide defined support areas for proper stabilization of a fractured bone. Plaster of Paris casts are somewhat less awkward than splints, and less susceptible to the misapplication of pressure than splints. Plaster of Paris casts do not, however, provide desirable definition of support areas for proper stabilization of a fractured bone. The problem encountered in providing for proper support areas is often due to a lack of visibility of the portion of the body to which the cast is being applied, and, all too often, the person applying the cast will provide for a support area much too close or too far removed from the sustained injury. Other disadvantages in using plaster of Paris casts are the length of time for the plaster to set, the weight of the cast, a tendency to maintain a moist condition next to a wound around which the cast is set, which, together with the difficulty in dressing such wounds, creates adverse conditions from a therapeutic standpoint. The cast produces patient discomfort and disagreeable odors due to the lack of ventilation, and the cast must be completely removed and replaced when swelling of the injured portion of the body occurs.

There has been a long felt need in the art to provide improved surgical and orthopedic supports which overcome the above mentioned disadvantages. In U.S. Pat. Nos. 2,308,483; 2,373,802; 2,384,804; and 2,489,253, methods and materials are disclosed for forming a cast by wrapping strips of material made of plastic about the injured member and bonding the strips of plastic together to form a unitary structure. The resulting cast is very similar in appearance to plaster of Paris casts, and, although the time needed for bonding the palstic material is considerably less than the setting time for plaster of Paris casts, the plastic casts exhibit all the other disadvantages inherent in plaster of Paris casts.

SUMMARY OF THE INVENTION

The invention provides a method and means for making light weight, compact, orthopedic splinting or bracing which provides proper stabilization of the portion of the body concerned with greater patient comfort. The splinting or bracing is adapted for easy, rapid, and less painful placement. A positive control for achieving proper support areas is provided, thereby allowing the person who is applying the splinting or bracing to provide an optimum support area with respect to the particular injury which has been sustained and to the particular portion of the body which has sustained the injury which is being treated. The splinting or bracing of this invention further provides optimum ventilation of the portion of the body being treated, and wounds associated with the sustained injury are readily available for dressing and visual surveillance by the doctor. In cases where swelling of the body portion being treated occurs, the splinting or bracing of this invention is quickly and easily adjusted without requiring complete replacement thereof. Unwanted moisture in proximity of any wound associated with the sustained injury, and sores due to undefined and uncontrolled support areas are completely avoided by the splinting or bracing of this invention.

In accordance with the present invention, orthopedic splinting or bracing is provided by applying a series of elongate splints of a relatively rigid plastic material to the injured part of the body member in mutually spaced, generally parallel relationship, so that the splints are positioned around the body part concerned and extend longitudinally thereof. Bands of perforated plastic material are applied about the series, transversely of the splints, for holding the splints in place, and the bands are secured to the splints giving support thereto and providing a straitjacketing structure for the body part concerned.

The bands of perforated plastic material can be of the nature of an adhesive tape in which the adhesive is capable of bonding with the plastic material of the splints, or the adhesive can be of the contact or pressure type which adheres to the plastic splints upon contact therewith. Preferably, however, the bands of perforated plastic material are formed by wrapping a perforated strip of plastic material around the splints, and the adhesive is an agent capable of bonding plastic to plastic. Such an agent is easily applied to the areas where the bands and the splints contact each other, and quickly bonds the plastic material in the bands to the plastic splints. The bonding agent is also applied to the strip of plastic material which has been wrapped on the splints to bond the overlying strips together forming a band. Bonding agents are available commercially which will form a rigid, secure bond between two plastic items in as little time as seven seconds.

In addition, preformed, perforated, plastic cuffs of various sizes and contours can be used to form the bands about the splints. The cuffs are molded in shapes corresponding to such parts of the body as the wrists, arms, necks, shoulders, chest, waist, hips, legs, and ankles. Various sizes of the cuffs of each shape allow for selection of a cuff of the right size for each specific application. The preformed cuffs are advantageously split longitudinally in two pieces, with respective sets of such pieces used to circumscribe the body part concerned and form the bands of material securing the splints. The opposing ends of the sets of cuffs can be secured together by an adhesive or bonding agent, or clasp means can be attached to the respective ends of the cuffs, whereby the ends can be held tightly together by the clasp means.

The bracing of this invention is particularly advantageous in allowing the orthopedic surgeon to periodically remove the bracing system from the patient during the long healing period to change dressings, make visual inspecting of the injured area, and to provide for more continuous sanitary conditions. When using split, preformed cuffs, approximately one-half of the splints of the brace are secured to one of the cuff pieces in each set; with the other splints being secured to the corresponding cuff piece in that set. To remove the brace, the corresponding cuff pieces in each set are disconnected, such as by disconnecting the clasp means which hold the cuffs together, and the two opposing halves of the brace removed from the patient. The bracing is replaced on the patient quickly and easily with a minimum of discomfort to the patient, by repositioning the two halves of the brace and reconnecting the corresponding cuff pieces in each set. When the plastic splints are held by strips of plastic material bonded thereto, rather than by the split cuffs, either the strips of material or the plastic splints are cut in strategic locations by a conventional cast cutting saw. The bracing is then temporarily removed to change dressings or whatever, and the bracing is then replaced on the patient. The members which were cut with the cast cutting saw are rebonded together quickly and easily with a minimum of patient discomfort.

When a wound is associated with the injury, as in the case of a compound fracture, the wound can often times be redressed and visually inspected by removing only one or two of the plastic splints rather than the entire bracing. The splints are easily rebonded in position after the wound has been redressed.

In many instances, casts or bracings, must be placed over a large portion of the body part concerned so as to encompass a joint therein, and, thus, immobilize the joint. For example, bracing may be required over the full length of the patients leg; in which case, the knee is immobilized. Movement of the immobilized joint is desirable during the long period of healing of the injured leg. Thus, following an initial healing period, in which the joint is immobilized by the orthopedic bracing, it is often desirable to replace the large, single piece brace with two smaller braces which are positioned on each side of the joint and are connected together by a hinge. The hinge allows for at least a minimal amount of movement of the joint during the remaining period in which the orthopedic bracing is needed. If a plaster of Paris cast is being used, the original, single-piece cast must be completely removed, and the two replacement casts formed in the conventional manner with the hinge positioned between the two new casts. The procedure is time consuming, discomforting to the patient, and expensive. In comparison, when using the orthopedic bracing of this invention, the plastic splints in the vicinity of the joint are removed. The removed splints are replaced with adjustable hinge members at respectively opposite sides of the joint which articulatively connect the two separate braces formed by the removal os said splints. The procedure is quick, easy, and inexpensive, with only minimal discomfort to the patient.

In those cases where the initial injury is of a nature such that the hinged section can be included in the bracing initially, one series of splints is applied to the body above the joint, and another series of splints is applied to the body below the joint. Bands of perforated plastic material are then applied to the splints as disclosed herein to provide straitjacketing structures above and below the joint respectively, and adjustable hinge means are connected to the straitjacketing structures at respectively opposite sides of the joint to articulatively interconnect the structures.

The splints can be made in various sizes and shapes to correspond to the different parts of the body to which they will be applied. The bands of perforated plastic material are preferably applied to the splints in selected, spaced positions therealong. The perforated nature of the bands and the open spaces between the splints provide exceptionally good ventilation for the portion of the body to which the splints have been applied.

THE DRAWING

Embodiments representing the best mode presently contemplated of carrying out the novel concepts of the invention in actual practice are illustrated in the accompanying drawing, in which:

FIG. 1 is a veiw showing bracing of this invention as applied to the lower section of a patient's leg;

FIG. 2, a view similar to that of FIG. 1, but showing a full lower limb brace comprising separate brace portions for the thigh and leg with a hinge member connecting the two braces;

FIG. 3, a veiw showing full arm bracing of this invention;

FIG. 4, a view showing bracing of this invention as a spica bracing about the body and left thigh of the patient;

FIG. 5, a perspective view of a roll of perforated, plastic material which is useful in forming the bands in the bracing of this invention;

FIG. 6, a perspective view of a preformed, split cuff which is useful in forming the bands in the bracing of this invention;

FIG. 7, a partial perspective view of the opposing ends of a preformed, split cuff showing clasp means for securing the opposing ends of the split cuff together;

FIG. 8, a perspective view of a hinge member which can be used to articulatively interconnect separate sections of bracing according to this invention;

FIG. 9, a perspective view of a heel piece which can be used in forming an ambulatory leg bracing according to this invention; and FIG. 10, a perspective of a straight, rigid strip of plastic which can be used in forming the splint pieces in the bracing of this invention.

DETAILED DESCRIPTION OF THE ILLUSTRATED EMBODIMENT

As illustrated in FIGS. 1–4, braces in accordance with the present invention are shown as applied to the upper and lower limbs as well as the central portion of the body of a patient. The braces are formed by applying around the part concerned a series of elongate splints 10 of a relatively rigid plastic material in mutually spaced relationship, so that the splints are positioned around the part concerned and extend longitudinally thereof. Bands 11 of perforated plastic material are applied about the series of splints 10 to hold the splints 10 in place. The bands 11 are secured to each of the splints 10 in the series to give support to the splints 10 and to provide an integral, straitjacketing structure for the body part concerned.

Figure 1:
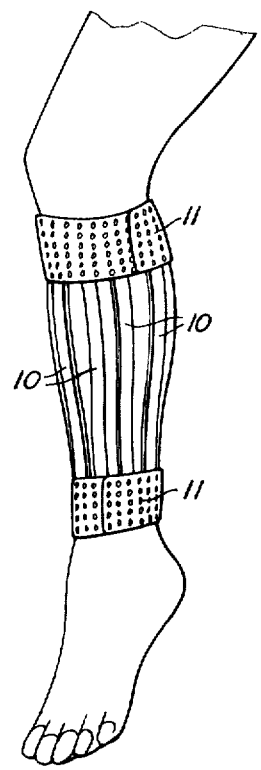

The bands 11 are applied about the series of splints 10 generally transverse of the splints 10. Preferably, the bands 11 are spaced apart in selected positions along the series of splints 10. In many cases the brace can be made with one series of splints, as shown in FIG. 1. In such instances, two bands 11 located at the opposite ends respectively of the series of splints 10 will generally suffice to hold the splints 10 in place and will provide sufficient support for the splints 10 to produce an integral, straitjacketing structure for the body part concerned. Of course, additional bands could be applied to the splints of the bracing shown in FIG. 1, for additional support for the splints 10 if such is desired.

Figure 2:
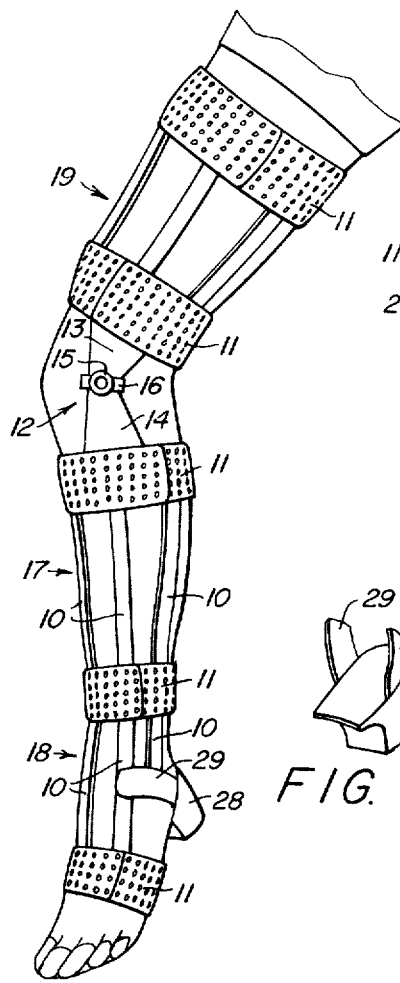
Figure 3:
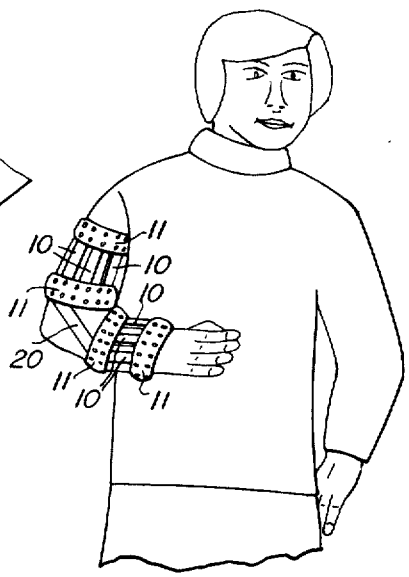
Figure 4:
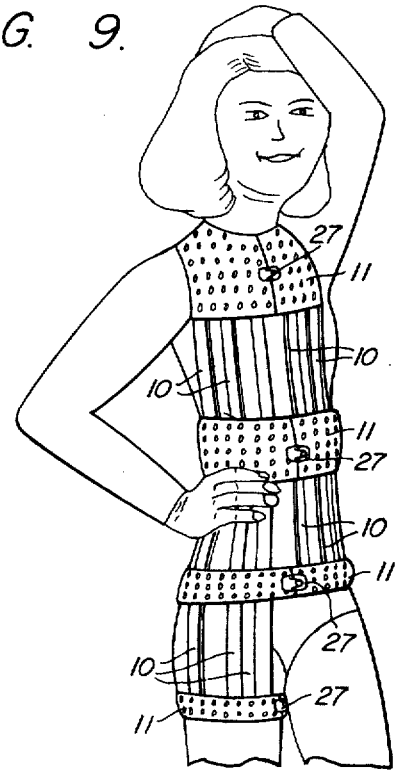

In many instances the brace is of such size or complexity that more than one series of splints is used. Examples of braces comprising more than one series of splints are shown in FIGS. 2–4. The brace illustrated in FIG. 2, encompasses the patient's full lower limb from the thigh to the ankle and instep of the patient's foot. The brace illustrated in FIG. 3, provides support for the brachium and forearm while simultaneously restraining them so as to prevent movement of the elbow. The spica brace shown in FIG. 4, encompasses the body of the patient from the neck to the waist, as well as extending to the patient's right thigh.

As shown in FIG. 2, the portion of the brace on the leg is formed by two sets of splints 17 and 18. The first set of splints 17 encompass the leg from about the knee to approximately the ankle with bands 11 of perforated plastic material secured to the splints 10 in set 17 at the respective ends thereof. The splints 10 in the second set of splints 18 are secured at one end thereof respectively to the band 11 adjacent the lower end of the first set of splints 17. The splints 10 in the second set of splints 18 extend from the ankle to the instep, and a third band 11 of perforated plastic material is secured about the ends of the splints 10. The two sets of splints, being secured by the three bands 11 provide a straitjacketing structure which supports the leg and the ankle.

The portion of the brace shown in FIG. 2, which supports the thigh, comprises a third set of splints 19, in which the splints 10 thereof are secured at their respective ends by two additional bands 11 of perforated plastic material. The portion of the brace supporting the thigh is articulatively connected to the other portion of the brace by hinge means, comprising the hinge member 12. Preferably, two hinge members 12 are connected to the bracing, the second being positioned on the opposite side of the knee and, thus, not visible in FIG. 2.

Figure 8:
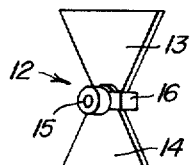

The hinge member 12, as shown in more detail in FIG. 8, comprises two, flat, generally triangular-shaped plates 13 and 14 which are pivotally interconnected at respective apexes thereof, so that the plates can pivot about an axis perpendicular to the plane of the plates and through the point of connection of the plates. Means can be associated with the hinge member 12 for adjusting the degree of pivotal movement of the plates 13 and 14. As shown, the offset stop arm 16 is adapted to be adjustably held by adjusting knob 15 in fixed position with respect to the lower plate 14. As the plate 13 pivots in a clockwise direction, it abuts the offset portion of stop arm 16. To reduce the degree of pivotal movement, stop arm 16 is adjusted to a position away from plate 13. The plates 13 and 14 are made of rigid plastic or of a material which can be bonded to the bands 11 of the brace structures of this invention.

In many cases, the orthopedic surgeon may not want to provide for pivotal movement of the joint initially, but, rather, to provide for the maximum degree of stabilization for the injured portions of the body on each side of the joint at least during the initial healing period. In such instances, the brace structure shown in FIG. 2, would have a series of splint members initially positioned around the knee in place of the hinge means 12, with the respective ends of the splints being bonded to the bands 11 above and below the knee. After the initial period of healing, the series of splints encompassing the knee are removed and replaced by the hinge means 12, as shown in FIG. 2.

In FIG. 3, a full arm bracing according to this invention is shown for supporting the right arm of the patient. Generally, the arm is to be held so that the forearm is restrained in a position approximately perpendicular to the brachium. As shown, a series of splints 10 is applied to the forearm, and bands 11 of plastic material are secured to the respective ends of the series of splints 10. A second series of splints 10 is applied to the brachium, and bands 11 of plastic material are secured to the respective ends of this series of splints 10. Plastic connecting members 20 (elongate members similar to the splints 10) are attached between the bands 11 on the opposing ends of the two series of splints respectively so as to hold the forearm in a position approximately perpendicular to the brachium. After an initial healing period, movement of the elbow can be provided for by replacing the connecting members 20 with a hinge member similar to that shown in FIG. 8. In the latter states of the healing period, it may be feasible, depending upon the exact nature of the injury to the arm, to remove one of the series of splints on either the brachium or forearm entirely, with the remaining series of splints providing adequate support for the remainder of the healing period.

Figure 5:
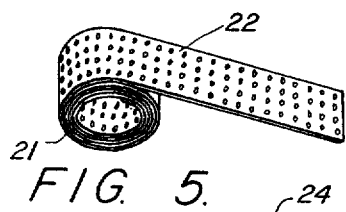

The bands 11 of perforated plastic material can be formed from a relatively thin, elongate strip of perforated plastic material which is wrapped about the series of splints 10 transversely of the splints. Advantageously, the strip of plastic material is supplied as roll 21, as shown in FIG. 5. The amount of plastic material needed to form a particular band is cut from the roll 21 and applied about the series of splints as shown in FIG. 1–3. The strip of plastic material in roll 21 has a plurality of perforations 22 extending along the length thereof.

Figure 6:
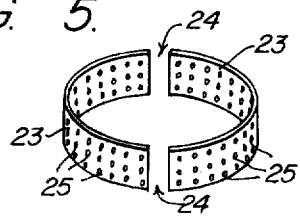

In many instances, it is also advantageous to use preformed cuffs 23, as shown in FIG. 6, in making the bands 11. Preferably, the preformed cuffs 23 are split as shown by reference numeral 24 in FIG. 6. The cuffs 23 are preformed in various sizes and contours to correspond to such parts of the body as the wrists, arms, necks, shoulder, chest, waist, hips, legs, and ankles. The preformed cuffs 23 have a plurality of perforations 25 distributed evenly thereabout.

The strip of plastic material such as shown in roll 21 of FIG. 5, can be in the form of an adhesive tape in which the adhesive, which is coated on one side of the strip of plastic material, is capable of bonding with the plastic material of the splints. The preformed cuffs, as shown in FIG. 6, can also be coated with an adhesive capable of bonding plastic to plastic. Preferably, however, both the strip of plastic material and the preformed cuffs are bonded to the plastic splints by a liquid adhesive which is applied to the plastic members at the desired points of contact between the members. There are various commercially available liquid adhesives which can be used for this purpose, including: acetone, sec-butyl alcohol, carbon disulfide, ethyl alcohol, methyl acetone, n-amyl acetate, m-amyl alcohol, "Cellosolve" acetate, diethyl "Cellosolve," isobutyl acetate, "Carbitol" acetate, benzyl "Cellosolve," acetylene dichloride, n-butylamine, ethyl acetate, methyl acetate, methyl ethyl ketone, methyl n-propyl ketone, diethyl ketone, amyl acetate (mixed isomers), "Cellosolve" methyl amyl acetate, tetrahydrofuran, and methyl "Cellosolve" acetate. "Carbitol" and "Cellosolve" are trade designations, but not proprietary trademarks, of products extensively used and known in industry. "Carbitol" is defined as, diethyleneglycol ethylether, and "Cellosolve" as, ethyleneglycol monoethylether. The choice of a liquid adhesive is dependent upon the particular plastic material used in making the splints 10 and perforated bands 11.

Figure 7:
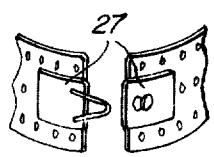

When the split, preformed cuffs, as shown in FIG. 6 are used in forming the bands 11 of perforated plastic material according to this invention, means are provided for securing the opposing ends of the cuffs tightly together to complete the straitjacketing structure of this invention. The ends of the preformed cuffs can be bonded together by means of an adhesive, such as those disclosed hereinabove, or the ends of the cuffs can be secured tightly together by means of clasps 27 which are bonded or otherwise attached to the cuffs as shown in FIG. 7.

A spica brace is shown in FIG. 4 in which four sets of split, preformed cuff pieces are advantageously used in forming the bands 11 of the straitjacketing structure. The first set of cuffs, having a contoured shape to fit securely over the shoulders and around the neck of the patient, is applied around the shoulders of the patient, and the mutually opposing ends of the cuffs are securely held together at the front and the back of the patient by clasps 27 (the back clasp not being visible). The second set of cuffs, having a contoured shape corresponding to the patient's torso, is positioned around the patient's trunk at approximately the midpoint between the patient's shoulders and waist. The mutually opposing ends of the secured set of cuffs are securely held together at the front and back of the patient by clasps 27 (the back clasp not being visible). The third set of cuffs having a contoured shape corresponding to the patient's waist, is positioned around the waist, and the mutually opposing ends thereof are securely held together at the front and back of the patient by clasps 27 (the back clasp not being visible). The body portion of the spica brace is completed by applying two sets of splints 10 around the patient's body in mutually spaced relationship so that the splints 10 extend longitudinally of the patient's body. The splints 10 in the first set thereof extend between the first and second sets of cuffs, with mutually opposite ends of the splints 10 being secured to the first and second sets of cuffs, respectively. The splints 10 in the second set thereof extend between the second and third sets of cuffs, with mutually opposite ends of the splints 10 being secured to the second and third sets, respectively. The leg portion of the spica brace is made by positioning a fourth set of split cuffs, having an appropriate preformed shape, to the patient's thigh, and securing the mutually opposing ends thereof together at the front and back of the patient by clasps 27 (the back clasp not being visible). A third series of splints 10 is applied to the patient's body in mutually spaced relationship so as to extend between the third and fourth sets of cuffs, with mutually opposite ends of the splints 10 being secured to the third and fourth sets of cuffs, respectively. The spica brace shown in FIG. 4, provides effective support for the torso and right hip of the patient.

The use of the split cuffs, which are secured together with the clasp means 27, is advantageous in allowing the orthopedic surgeon to periodically remove the brace from his patient to change dressings, to make visual inspections of the injured area, etc. The spica brace shown in FIG. 4, is easily removed from the patient by simply disconnecting the clasps 27 which hold the respective sets of cuffs together. The separate sections of the cuffs on the left and right-hand sides of the patient's body, together with the splints 10 which are connected thereto, can then be removed from the paitent without destroying any portion of the brace. The brace is repositioned on the patient quickly and easily by repositioning the separate halves of the brace and reconnecting the clasps 27 to securely hold the respective sets of cuffs together.

Figure 9:
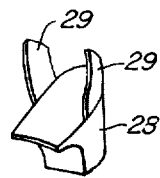

Another advantageous feature of the bracing of this invention is illustrated in FIGS. 2 and 9. Oftentimes, a heel section is desirably built into a leg brace such as that shown in FIG. 2, to provide ambulatory use of the leg by the patient. With the bracing of this invention, plastic heel sections 28, such as shown in detail in FIG. 9, can be molded having extensions 29. The heel section 28 is positioned as shown in FIG. 2, and the extensions 29 are firmly secured to the splint members 10.

Figure 10:

The splint members 10 are conveniently made from straight sections of elongate, plastic bars 30 as shown in FIG. 10. The bars 30 can be shaped to conform to the contour of the body part to which it will be applied as a splint 10. For example, the bar 30 could be heated and shaped to conform to the calf of the patient's leg when being used in a brace such as shown in FIG. 1. In addition to the straight bars 30, preshaped splint members could be supplied to the orthopedic surgeon in a number of shapes and sizes from which he could select correct splints for any particular application.

The splints, strips of perforated material, and split cuff members can be made from any rigid plastic material. Representative plastic materials which can be used in making the different parts of the bracing of this invention include polyethylene, polypropylene, acrylics, acetals, nylons, cellulosics, ABS, vinyl polymers, polyurethanes, phenolics, polyesters, polystyrenes, ethylene-vinyl acetates, polycarbonates, polysulfones, alkyds, allyls, and amino based polymers.

Bracing of the present invention can be applied to the patient in a very short time due to the rapid bonding of the plastic components. There is no setting time following the application of the braces of this invention, and, thus, the period of time which the patient must be kept under anaesthethic is very short. Due to the perforated nature of the bonds, and the open spaces between the splints, the bracing of this invention provides for exceptional ventilation of the portion of the body to which the bracing is applied. The open spaces also provide the orthopedic surgeon with direct visual observation of the placement of the bracing. Thus, precise definition of the support area can be achieved, and the chances of gaining a support area too close or too far away from the injury is minimized.

I claim:

1. A method of applying orthopedic splints or bracing, comprising applying to the part of the body concerned, a series of elongate splints of a relatively rigid plastic material in mutually spaced relationship so the splints extend longtudinally of the body part concerned; applying about said series, transversely of said splints, bands of perforated plastic material for holding said splints in place; and securing said bands to said splints by an adhesive agent at the points of contact between the bands and the splints, said adhesive agent being capable of bonding the plastic material of the splints to the plastic of the perforated bands, whereby said bands support said splints and the splints and bands together provide a straitjacketing structure for said body part concerned.

2. A method in accordance with claim 1, wherein the bands of perforated plastic are applied to the splints in selected, spaced positions therealong.

3. A method in accordance with claim 1, wherein the bands of perforated plastic material are of the nature of an adhesive tape in which the adhesive agent is coated on one side of the bands.

4. A method in accordance with claim 1, wherein the bands are secured to said splints by applying a liquid adhesive agent to the points of contact between the bands and the splints, said agent being capable of bonding plastic to plastic.

5. A method in accordance with claim 1, wherein the bands of perforated plastic material are a pair of perforated cuffs being substantially semi-circular in shape so as to conform to the body part to which applied, and means are provided for joining the opposing ends of said pair of cuffs so that the pair of cuffs circumscribe said body part.

6. A method in accordance with claim 5, wherein the opposing ends of said cuffs are secured tightly together by means of clasps.

7. A method in accordance with claim 5, wherein the opposing ends of said cuffs are secured tightly together by an adhesive or a bonding agent.

* * * * *